US010863921B2

(12) United States Patent
Gigi

(10) Patent No.: US 10,863,921 B2
(45) Date of Patent: Dec. 15, 2020

(54) METHOD AND APPARATUS FOR DETERMINING A RESPIRATION RATE OF A SUBJECT

(71) Applicant: KONINKLIJKE PHILIPS N.V., Eindhoven (NL)

(72) Inventor: Ercan Ferit Gigi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 283 days.

(21) Appl. No.: 15/775,096

(22) PCT Filed: Nov. 15, 2016

(86) PCT No.: PCT/EP2016/077741
§ 371 (c)(1),
(2) Date: May 10, 2018

(87) PCT Pub. No.: WO2017/085062
PCT Pub. Date: May 26, 2017

(65) Prior Publication Data
US 2018/0325420 A1    Nov. 15, 2018

(30) Foreign Application Priority Data

Nov. 20, 2015    (EP) .................................... 15195548

(51) Int. Cl.
*A61B 5/08*       (2006.01)
*A61B 5/113*      (2006.01)
*A61B 5/00*       (2006.01)

(52) U.S. Cl.
CPC .......... *A61B 5/0816* (2013.01); *A61B 5/1135* (2013.01); *A61B 5/6823* (2013.01); *A61B 2562/0219* (2013.01)

(58) Field of Classification Search
CPC .. A61B 5/08; A61B 5/00; A61B 5/113; A61B 5/0816; A61B 5/1135; A61B 5/6823; A61B 2562/0219
See application file for complete search history.

(56) References Cited

U.S. PATENT DOCUMENTS 6,162,183 A * 12/2000 Hoover ................ A61B 5/1135
                                                  600/534
6,741,885 B1    5/2004 Park et al.
7,435,221 B1   10/2008 Bharmi et al.
(Continued)

OTHER PUBLICATIONS

International Search Report and Written Opinion for PCT/EP2016/077741, dated Feb. 24, 2017, pp. 1-11.

*Primary Examiner* — Eric J Messersmith

(57) ABSTRACT

According to an aspect, there is provided a method of determining the respiration rate of a subject, the method comprising obtaining a signal from a sensor that is worn or carried by the subject; analyzing the signal to determine a plurality of values for a breathing-related feature; forming a histogram from the plurality of values for the breathing-related feature, the histogram comprising a plurality of groups, with each group having an associated count that is the number of occurrences of a value or values for the breathing-related feature corresponding to the group; applying a weighting to the count associated with each group to form weighted counts; and determining the respiration rate from a mean of the histogram with the weighted counts.

13 Claims, 10 Drawing Sheets

(56) References Cited

U.S. PATENT DOCUMENTS

| | | |
|---|---|---|
| 2006/0241510 A1 | 10/2006 | Halperin et al. |
| 2007/0073169 A1 | 3/2007 | Averina et al. |
| 2007/0073181 A1 | 3/2007 | Pu et al. |
| 2007/0135725 A1* | 6/2007 | Hatlestad ............ A61B 5/0809 600/529 |
| 2008/0312541 A1 | 12/2008 | Lewicke et al. |
| 2010/0298732 A1 | 11/2010 | Zhang et al. |
| 2012/0029375 A1 | 2/2012 | Lane et al. |
| 2013/0030257 A1* | 1/2013 | Nakata ................. A61B 5/4818 600/301 |
| 2014/0194793 A1 | 7/2014 | Nakata et al. |
| 2014/0228692 A1 | 8/2014 | Chan et al. |

\* cited by examiner

METHOD AND APPARATUS FOR DETERMINING A RESPIRATION RATE OF A SUBJECT

This application is the U.S. National Phase application under 35 U.S.C. § 371 of International Application No. PCT/EP2016/077741, filed on Nov. 15, 2016, which claims the benefit of European Application Serial No. 15195548.1, filed Nov. 20, 2015. These applications are hereby incorporated by reference herein.

TECHNICAL FIELD OF THE INVENTION

The invention relates to a method and apparatus for determining a respiration rate of a subject.

BACKGROUND OF THE INVENTION

In various situations it is useful to know the respiration rate of a subject. The so-called 'golden reference' for respiration measurement is a manual count by a trained clinician. The clinician visually inspect the subject's (e.g. child's) chest and belly for respiratory motions. Ideally the counting should last a full minute. The inhalation and exhalation make up one breath. The number of breaths counted during one minute gives the respiratory rate in respirations per minute (RPM).

Various devices are available that enable the breathing rate (respiratory rate) of a subject to be determined. Some devices use an accelerometer (also referred to as a 3D accelerometer) that is worn on the chest or belly of the subject and that measures motion of the chest or belly in terms of accelerations in three dimensions. The 3D accelerometer signal can be processed, for example, such that the breathing rate is inferred by analyzing angular changes (represented on a 2D plane in space) of the signal. Such devices are minimally intrusive, consumes little energy and is easy to apply or be worn by the subject.

Other devices measure the respiratory rate from other vital signs of the subject or other characteristics of the motion of the subject. For example, some devices can measure the respiratory rate from changes in the blood oxygen level (SpO2), changes in the heart rate, breath motions from a video signal, breath sounds from a microphone, airflow through the nose, a band around the chest that measures volumetric change of the lungs, etc.

The existing devices tend to provide satisfactory detection of respiratory rates in adults, but do not provide reliable detection of respiratory rates in children. This can be due to children breathing more frequently and faster than adults, more irregularly than an adult, children having a similar inhale/exhale duration period, and children moving a lot during the measurement.

Therefore there is a need for an improved method and apparatus for determining a respiration rate of a subject, particularly children.

SUMMARY OF THE INVENTION

According to a first aspect, there is provided a method of determining the respiration rate of a subject, the method comprising obtaining a signal from a sensor that is worn or carried by the subject; analyzing the signal to determine a plurality of values for a breathing-related feature; forming a histogram from the plurality of values for the breathing-related feature; and determining the respiration rate from a weighted average center of the histogram.

In some embodiments, each value of the breathing-related feature is a candidate respiration rate, and wherein the step of analyzing comprises analyzing the signal to determine a plurality of candidate breath periods, wherein each candidate breath period corresponds to the time between each candidate breath by the subject; and determining the plurality of candidate respiration rates from the plurality of candidate breath periods.

In alternative embodiments, each value of the breathing-related feature is a candidate breath period, wherein each candidate breath period corresponds to the time between each candidate breath by the subject, and wherein the step of determining the respiration rate comprises determining an estimated breath period from the weighted average center of the histogram; and determining the respiration rate from the estimated breath period.

In some embodiments the step of forming a histogram comprises grouping the values for the breathing-related feature into a plurality of groups based on the values for the breathing-related feature.

In some embodiments the step of forming a histogram further comprises discarding from the histogram any group having less than a threshold number of values in the group.

In some embodiments the step of determining the respiration rate comprises using non-linear compression on the number of values in each of the groups to give an enhanced number of values in each of the groups; and determining the respiration rate from a weighted average center of a histogram formed using the enhanced number of values in each of the groups.

In some embodiments the method further comprises the step of discarding any values for the breathing-related feature that do not meet a quality criterion.

In some embodiments the step of analyzing the signal to determine a plurality of values for a breathing-related feature comprises identifying zero-crossings in the signal; and determining a value for the breathing-related feature from the time between consecutive zero-crossings.

In some embodiments the step of analyzing the signal to determine a plurality of values for a breathing-related feature comprises identifying peaks and/or troughs in the signal; and determining a value for the breathing-related feature from the distance between consecutive peaks and/or troughs.

In some embodiments the step of analyzing the signal to determine a plurality of values for a breathing-related feature comprises performing a spectral analysis of the signal.

In alternative embodiments, the step of analyzing the signal to determine a plurality of values for a breathing-related feature comprises analyzing the phase of the signal.

In some embodiments the sensor is an accelerometer and the signal is an acceleration signal. In alternative embodiments the sensor is a sensor that measures the heart rate of the subject. In other alternative embodiments, the sensor is a sensor that measures the sound of the subject breathing. In other alternative embodiments, the sensor is a sensor that measures the air flow into and/or out of the body of the subject.

According to a second aspect, there is provided a computer program product comprising a computer readable medium having computer readable code embodied therein, the computer readable code being configured such that, on execution by a suitable computer or processor, the computer or processor is caused to perform any of the methods described above.

According to a third aspect, there is provided an apparatus for determining the respiration rate of a subject, the apparatus comprising a processing unit configured to receive a signal from a sensor; analyze the signal to determine a plurality of values for a breathing-related feature; form a histogram from the plurality of values for the breathing-related feature; and determine the respiration rate from a weighted average center of the histogram.

In some embodiments, each value of the breathing-related feature is a candidate respiration rate, and wherein the processing unit is configured to analyze the signal to determine a plurality of candidate breath periods, wherein each candidate breath period corresponds to the time between each candidate breath by the subject; and to determine the plurality of candidate respiration rates from the plurality of candidate breath periods.

In alternative embodiments, each value of the breathing-related feature is a candidate breath period, wherein each candidate breath period corresponds to the time between each candidate breath by the subject, and wherein the processing unit is configured to determine the respiration rate by determining an estimated breath period from the weighted average center of the histogram; and determine the respiration rate from the estimated breath period.

In some embodiments the processing unit is configured to form a histogram by grouping the values for the breathing-related feature into a plurality of groups based on the values for the breathing-related feature.

In some embodiments the processing unit is further configured to form the histogram by discarding from the histogram any group having less than a threshold number of values in the group.

In some embodiments the processing unit is configured to determine the respiration rate by using non-linear compression on the number of values in each of the groups to give an enhanced number of values in each of the groups; and determine the respiration rate from a weighted average center of a histogram formed using the enhanced number of values in each of the groups.

In some embodiments the processing unit is further configured to discard any values for the breathing-related feature that do not meet a quality criterion.

In some embodiments the processing unit is configured to analyze the signal to determine a plurality of values for a breathing-related feature by identifying zero-crossings in the signal; and to determining a value for the breathing-related feature from the time between consecutive zero-crossings.

In some embodiments the processing unit is configured to analyze the signal to determine a plurality of values for a breathing-related feature by identifying peaks and/or troughs in the signal; and determining a value for the breathing-related feature from the distance between consecutive peaks and/or troughs.

In some embodiments the processing unit is configured to analyze the signal to determine a plurality of values for a breathing-related feature by performing a spectral analysis of the signal.

In alternative embodiments, the processing unit is configured to analyze the signal to determine a plurality of values for a breathing-related feature by analyzing the phase of the signal.

In some embodiments the apparatus further comprises the sensor. In some embodiments the sensor is an accelerometer and the signal is an acceleration signal. In alternative embodiments the sensor is a sensor that measures the heart rate of the subject. In other alternative embodiments, the sensor is a sensor that measures the sound of the subject breathing. In other alternative embodiments, the sensor is a sensor that measures the air flow into and/or out of the body of the subject.

According to a fourth aspect, there is provided a method of determining the respiration rate of a subject, the method comprising obtaining a signal from a sensor that is worn or carried by the subject; analyzing the signal to determine a plurality of values for a breathing-related feature; forming a histogram from the plurality of values for the breathing-related feature, the histogram comprising a plurality of groups, each group corresponding to one or more possible values of the breathing-related feature, with each group having an associated count that is the number of occurrences of a value or values for the breathing-related feature corresponding to the group; applying a weighting to the count associated with one or more groups to form weighted counts; and determining the respiration rate from a mean of the histogram with the weighted counts.

The above method is particularly useful for determining the respiration rate for children who often do not always breathe calmly around a single rate during a measurement procedure. Small children can breathe fast and slow during a measurement, and thus selecting the maximally encountered rate (e.g. the peak in the histogram) would not always provide the most appropriate respiration rate. In addition, motion artefacts in the sensor signal may result in counts in the histogram and thus simply taking the mean of the histogram would allow these artefacts to influence the result. Instead, the method provides that one or more counts of the histogram are weighted before the mean of the histogram with the weighted counts is determined. This mean provides the respiration rate. Thus the method allows multiple peaks in the histogram (e.g. two or more rates at which the subject was breathing during the measurement) to influence the result, thereby improving the reliability of the obtained respiration rate.

In some embodiments, the step of determining the respiration rate from the mean of the histogram comprises determining the mean of the histogram by (i) for each group, multiplying a value for the breathing-related feature corresponding to the group by the weighted count for the group; (ii) summing the result of (i) for each group; (iii) dividing the result of (ii) by the sum of the weighted counts.

In some embodiments, each value of the breathing-related feature is a candidate respiration rate, and wherein the step of analyzing comprises analyzing the signal to determine a plurality of candidate breath periods, wherein each candidate breath period corresponds to the time or distance between each candidate breath by the subject; and determining the plurality of candidate respiration rates from the plurality of candidate breath periods.

In alternative embodiments, each value of the breathing-related feature is a candidate breath period, wherein each candidate breath period corresponds to the time or distance between each candidate breath by the subject, and wherein the step of determining the respiration rate comprises determining an estimated breath period from the mean of the histogram; and determining the respiration rate from the estimated breath period.

In some embodiments, the step of analyzing the signal to determine a plurality of values for a breathing-related feature comprises identifying zero-crossings in the signal; and determining a value for the breathing-related feature from the time between consecutive zero-crossings.

In alternative embodiments, the step of analyzing the signal to determine a plurality of values for a breathing-related feature comprises identifying peaks and/or troughs in the signal; and determining a value for the breathing-related feature from the distance between consecutive peaks and/or troughs.

In some embodiments, the step of applying a weighting to the count associated with one or more groups comprises applying a weighting such that the mean of the histogram is weighted towards the value or values of the breathing-related feature for the group having the highest count.

In further or alternative embodiments, the step of applying a weighting to the count associated with one or more groups comprises applying a weighting such that the value or values of the breathing-related feature for the group or groups having the highest counts are emphasized in the mean of the histogram.

In some embodiments, the step of applying a weighting to the count associated with one or more groups comprises discarding from the histogram any group having a count that is less than a threshold number.

In alternative embodiments, the step of applying a weighting to the count associated with one or more groups comprises determining the weighted count for each group as the nth power of the respective count, where n is any number greater than 1.

In alternative embodiments, the step of applying a weighting to the count associated with one or more groups comprises determining the weighted count for each group by subtracting a threshold value from the respective count; wherein a weighted count is set to zero in the event that the threshold value is equal to or greater than the respective count. In some embodiments, the threshold value is determined as a fraction of the highest count.

According to a fifth aspect, there is provided a computer program product comprising a computer readable medium having computer readable code embodied therein, the computer readable code being configured such that, on execution by a suitable computer or processor, the computer or processor is caused to perform any of the method embodiments according to the fourth aspect.

According to a sixth aspect, there is provided an apparatus for determining the respiration rate of a subject, the apparatus comprising a processing unit configured to receive a signal from a sensor; analyze the signal to determine a plurality of values for a breathing-related feature; form a histogram from the plurality of values for the breathing-related feature, the histogram comprising a plurality of groups, each group corresponding to one or more possible values of the breathing-related feature, with each group having an associated count that is the number of occurrences of a value or values for the breathing-related feature corresponding to the group; apply a weighting to the count associated with one or more groups to form weighted counts; and determine the respiration rate from a mean of the histogram with the weighted counts.

The above apparatus is particularly useful for determining the respiration rate for children who often do not always breathe calmly around a single rate during a measurement procedure. Small children can breathe fast and slow during a measurement, and thus selecting the maximally encountered rate (e.g. the peak in the histogram) would not always provide the most appropriate respiration rate. In addition, motion artefacts in the sensor signal may result in counts in the histogram and thus simply taking the mean of the histogram would allow these artefacts to influence the result. Instead, the apparatus provides that one or more counts of the histogram are weighted before the mean of the histogram with the weighted counts is determined. This mean provides the respiration rate. Thus the apparatus allows multiple peaks in the histogram (e.g. two or more rates at which the subject was breathing during the measurement) to influence the result, thereby improving the reliability of the obtained respiration rate.

In some embodiments, the processing unit is configured to determine the respiration rate from the mean of the histogram by (i) for each group, multiplying a value for the breathing-related feature corresponding to the group by the weighted count for the group; (ii) summing the result of (i) for each group; (iii) dividing the result of (ii) by the sum of the weighted counts.

In some embodiments, each value of the breathing-related feature is a candidate respiration rate, and wherein the processing unit is configured to analyze the signal by analyzing the signal to determine a plurality of candidate breath periods, wherein each candidate breath period corresponds to the time or distance between each candidate breath by the subject; and determine the plurality of candidate respiration rates from the plurality of candidate breath periods.

In alternative embodiments, each value of the breathing-related feature is a candidate breath period, wherein each candidate breath period corresponds to the time or distance between each candidate breath by the subject, and wherein the processing unit is configured to determine the respiration rate by determining an estimated breath period from the mean of the histogram; and determining the respiration rate from the estimated breath period.

In some embodiments, the processing unit is configured to analyze the signal to determine a plurality of values for a breathing-related feature by identifying zero-crossings in the signal; and determining a value for the breathing-related feature from the time between consecutive zero-crossings.

In alternative embodiments, the processing unit is configured to analyze the signal to determine a plurality of values for a breathing-related feature by identifying peaks and/or troughs in the signal; and determining a value for the breathing-related feature from the distance between consecutive peaks and/or troughs.

In some embodiments, the processing unit is configured to apply a weighting to the count associated with one or more groups such that the mean of the histogram is weighted towards the value or values of the breathing-related feature for the group having the highest count.

In some embodiments, the processing unit is configured to apply a weighting to the count associated with one or more groups such that the value or values of the breathing-related feature for the group or groups having the highest counts are emphasized in the mean of the histogram.

In some embodiments, the processing unit is configured to apply a weighting to the count associated with one or more groups by discarding from the histogram any group having a count that is less than a threshold number.

In alternative embodiments, the processing unit is configured to apply a weighting to the count associated with one or more groups by determining the weighted count for each group as the nth power of the respective count, where n is any number greater than 1.

In alternative embodiments, the processing unit is configured to apply a weighting to the count associated with one or more groups by determining the weighted count for each group by subtracting a threshold value from the respective count; wherein a weighted count is set to zero in the event that the threshold value is equal to or greater than the respective count. In some embodiments, the threshold value is determined as a fraction of the highest count.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
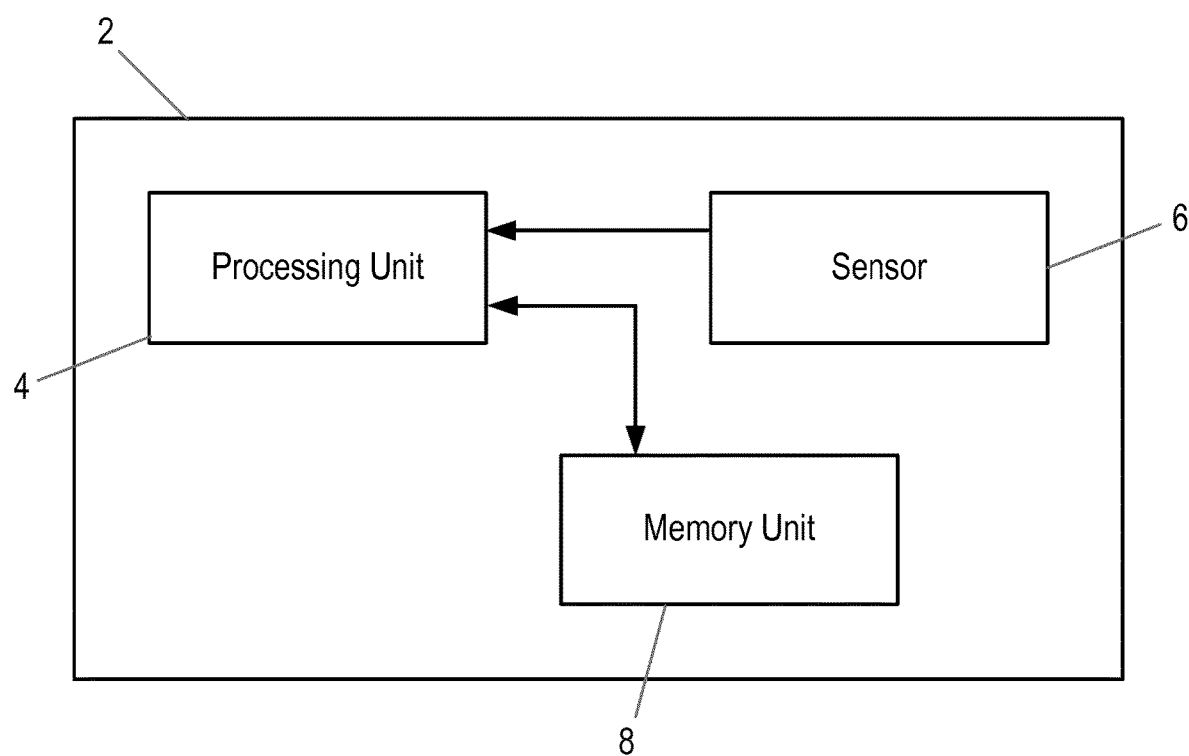
FIG. 1 shows an embodiment of an apparatus according to an aspect of the invention.

FIG. 1 is a block diagram of an embodiment of an apparatus 2 according to an aspect of the invention. The apparatus 2 comprises a processing unit 4 that controls the operation of the apparatus 2 and that can implement the respiration rate measurement method. The processing unit 4 is configured or adapted to process a signal from a sensor 6 that is used to monitor a part of the body of the subject and to process the sensor signal to determine the respiration rate of the subject. The processing unit 4 can comprise one or more processors, control units, multi-core processors or processing modules that are configured or programmed to control the apparatus 2 to determine the respiration rate of a subject as described below.

In some embodiments the apparatus 2 can be worn or carried by the subject. Preferably, the sensor is a sensor that measures the movements or other motion of the subject. For example, the sensor can be an accelerometer that can be worn or carried on the chest of the subject and that measures accelerations in three dimensions, a gyroscope that measures changes in rotation and orientation, a camera that records images of the subject's upper body as they breathe or a band that is worn around the chest that outputs a signal that represents the volumetric change of the subject's lungs. Alternatively the sensor can be a sensor that measures a vital sign or physiological characteristic (other than respiration rate) that is affected by the subject's breathing. For example, the sensor can be a sensor for measuring heart rate, such as a photoplethysmographic (PPG) sensor, a sensor for measuring blood oxygen level, such as an SpO2 sensor, a sensor that measures breath sounds (e.g. a microphone), a sensor that measures the temperature of air in the nose or mouth, a sensor that measures changes in skin color, or a sensor for measuring the flow of air through the subject's mouth or nose. Those skilled in the art will be aware of other types of sensors that can be used in an apparatus 2 according to the invention.

In the case of an accelerometer, the accelerometer can measure the accelerations along three orthogonal axes (e.g. labelled X, Y and Z) and output three signals, each representing the accelerations along a respective one of the axes.

The sensor can be part of the apparatus 2 or separate from the apparatus 2. In the embodiment of FIG. 1, the processing unit 4 and the sensor 6 are shown as being part of the same piece of apparatus. It will be appreciated that the sensor 6 and processing unit 4 can be provided in separate housings or devices, and they can be provided with appropriate circuitry or components to enable the measurement signal to be sent from the sensor 6 to the processing unit 4. For example where the sensor 6 is an accelerometer, the accelerometer can be worn on or near the chest of the subject, and the processing unit 4 can be part of a smartphone or other electronic device that the subject carries in their pocket or hand, in which case the signal from the accelerometer can be sent wirelessly to the processing unit 4 in the smartphone or other device so that the respiration rate can be determined.

In some embodiments the processing unit 4 can receive a signal directly from the sensor 6 and the processing unit 4 can process this signal in real-time or near real-time in order to determine the respiration rate of the subject. In other embodiments (including embodiments where the sensor 6 is separate from the apparatus 2), a signal from a or the sensor 6 can be stored in a memory unit 8 and the processing unit 4 can retrieve and analyze the previously-obtained sensor measurements from the memory unit 8 when the respiration rate of the subject is to be determined.

The memory unit 8 can be used for storing program code that can be executed by the processing unit 4 to perform the method described herein. The memory unit 8 can also be used to store signals and measurements made or obtained by the or a sensor during operation.

As noted above, in some embodiments the processing unit 4 may be part of a smart phone or other general purpose computing device that can be connected to or otherwise receive a measurement signal from a sensor 6, but in other embodiments the apparatus 2 can be an apparatus that is dedicated to the purpose of measuring the respiration rate of a subject. In embodiments where the processing unit 4 is part of a smart phone or other general purpose computing device, the sensor 6 could be a sensor that is integrated into the smart phone, or a sensor that is separate to the smart phone and that can provide sensor signals/measurements to the smart phone/computing device for processing and analysis (for example via a wired or wireless connection).

It will be appreciated that in some embodiments the apparatus 2 can make use of multiple sensors 6 (of the same or different types) to monitor the subject that can each be processed by processing unit 4 to improve the reliability of the respiration rate measurement.

It will be appreciated that FIG. 1 only shows the components required to illustrate this aspect of the invention, and in a practical implementation the apparatus 2 will comprise additional components to those shown. For example, the apparatus 2 may comprise a battery or other power supply for powering the apparatus 2, a communication module for enabling the measurements of the respiration rate of the subject to be communicated to a base unit for the apparatus 2 or a remote computer, and/or one or more user interface components that allow the subject or another user to interact and control the apparatus 2. As an example, the one or more user interface components could comprise a switch, a button or other control means for activating and deactivating the apparatus 2 and/or respiration rate measurement process. The user interface components can also or alternatively comprise a display or other visual indicator for providing information to the subject and/or other user about the operation of the apparatus 2, including displaying the measurements of the respiration rate.

Figure 2:
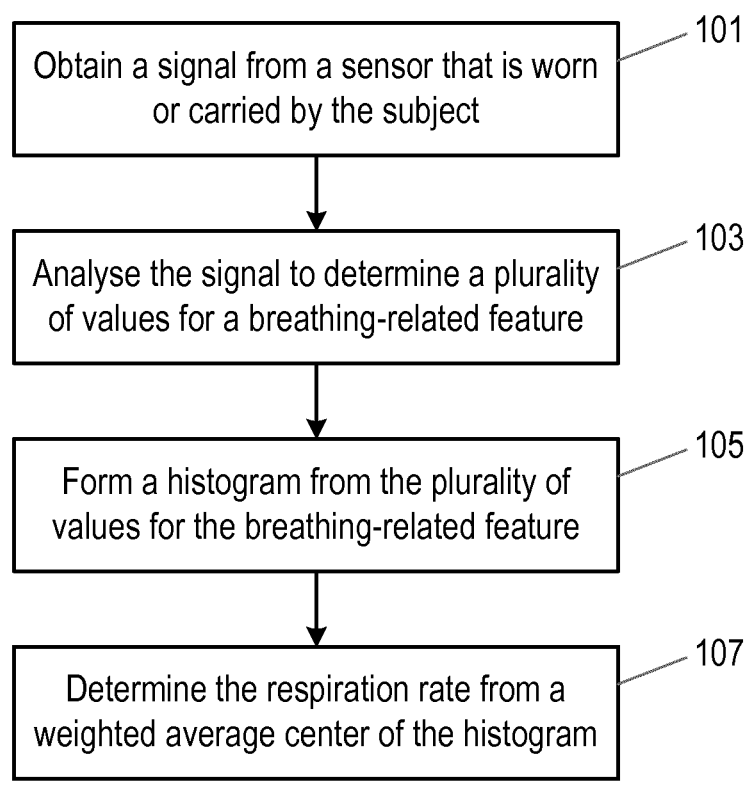
FIG. 2 is a flow chart illustrating a method of determining the respiratory rate.

The flow chart in FIG. 2 illustrates a general method of determining the respiratory rate according to an aspect of the invention. Briefly, the method according to the invention makes use of one or more histograms for determining the respiratory rate (where a histogram is a function that counts the number of observations that fall into each of a number of disjoint categories (known as bins or groups)).

In a first step of the method, step 101, a signal from a sensor 6 that is worn or carried by the subject is obtained. The signal can be obtained in real-time from the sensor 6, or obtained from a memory unit 8 in which a previously-obtained signal has been stored.

In preferred embodiments the sensor 6 is an accelerometer and the signal is an acceleration signal that represents the acceleration measured by the accelerometer in three dimensions (e.g. that comprises three signals, each representing the acceleration along one of the measurement axes of the accelerometer). Alternatively the sensor 6 can comprise another type of motion or movement sensor, such as a gyroscope, camera (the images from which can be analyzed to identify movements due to breathing) or band for measuring volumetric changes in the subject's lungs. Alternatively, the sensor is a sensor that measures a vital sign or physiological characteristic, such as the heart rate of the subject, the blood oxygen level of the subject, the sound of the subject breathing, the temperature of air in the nose or mouth, the color of the skin, or the air flow into and/or out of the body of the subject.

In step 103, the signal from the sensor 6 is analyzed to determine a plurality of values for a breathing-related feature. The signal can be analyzed in real-time, i.e. as the signal is measured by the sensor 6, or a segment of the obtained signal can be analyzed. With any of the exemplary sensors 6 described above there will be a strong correlation of the periodicity in the signal with the observed breathing rate. The breathing-related feature is a feature of the signal that is associated with the breathing of the subject and that should appear or be found throughout the signal and that can be generally correlated with a part of the breathing cycle of the subject. For example the part of the breathing cycle can correspond to the start of the inhalation, the end of the inhalation, the start of the exhalation, the end of the exhalation, etc.

In some embodiments each value of the breathing-related feature is a candidate breath period, with each value being an estimate of the duration of a breath that is based on the time or distance between two similar consecutive parts of the signal. This analysis can be performed in the time domain, the analysis can be a spectral analysis, for example in which the signal is converted to the frequency domain (e.g. using a Fourier transform), or the analysis can be an analysis of signal phase.

Depending on the type of sensor 6 used to obtain the sensor signal, the similar consecutive parts of the signal can be the time or distance between consecutive zero-crossings of the signal, the time or distance between points where the signal has a certain amplitude, the time or distance between consecutive peaks (local maxima) of the signal, the time or distance between consecutive troughs/valleys (local minima) of the signal, the time or distance between consecutive peaks (local maxima) and/or troughs (local minima) of the signal.

As noted above, in some embodiments an analysis of signal phase can be used to determine the candidate breath periods. In that case any chosen phase can be used to mark a period start. For example, by using an 'analytical signal' obtained through a Hilbert transformation, it is possible to derive the phase of each sample of the sensor signal. If zero-crossings are used to identify the breath periods, these would correspond to a phase of 0 or 180 degrees. A peak would correspond to 90 degrees and a trough/valley to 270 degrees. However with local phase information as a companion signal at hand, any arbitrary phase between 0 and 360 degrees can be used instead.

In alternative embodiments, each value of the breathing-related feature is a candidate respiration rate, with each value being an estimate of the duration of a breath that is based on the time or distance between two similar consecutive parts of the signal. Each candidate respiration rate can be determined by determining candidate breath periods as described above, with each candidate respiration rate corresponding to the inverse of a respective candidate breath period.

It will be appreciated that the breathing-related feature to be identified in the signal can depend on the nature of the signal (e.g. acceleration signal, heart rate signal, air flow signal, etc.) and how the breathing cycle of the subject affects that type of measurement.

For example, in the case of an accelerometer 6 that is positioned on the chest of the subject, the acceleration signal will contain a generally sinusoidal component corresponding to the movements of the chest due to breathing (with varying periodicity corresponding to changes in respiration rate), and the analysis in step 103 identifies the breathing-related feature as a characteristic of that breathing component.

Of course it will be appreciated that the acceleration signal will also contain accelerations due to other movements by the subject, and at this stage of the processing, it is not clear which parts of the signal relate to the breathing of the subject and which parts relate to other movements or characteristics of the subject, particularly those that have a similar frequency to the breathing of the subject. Thus, unless the acceleration signal is 'clean' (i.e. the accelerations in the signal are solely due to breathing movements) the values determined in step 103 will include values derived from parts of the signal that do not correspond to parts of the breathing cycle of the subject. For example, where the time or distance between consecutive zero-crossings of the signal is used to determine each value of the breathing-related feature, zero-crossings caused by other movements or motions will contribute to the values determined in step 103. A similar situation will occur with signals from other types of sensors and/or with values for a breathing-related feature derived in a different way (e.g. those based on peaks in the signal, or peaks in the frequency domain).

In the case of a sensor other than an accelerometer, a signal similar to an acceleration signal can be derived after suitable (e.g. band-pass) filtering. For example an air flow sensor will provide an air pressure/flow signal that will also exhibit peaks that are correlated with the breathing cycle. In the case of a camera, analysis of the video of the chest area could provide a signal representing the displacement of a region of interest along a certain direction. This displacement signal will also show peaks, correlated with the breathing cycle. With a PPG sensor the variation of the amplitude of the pulse rate (related to the heart beat) can be used to measure local breath durations. A temperature sensor in the nose would also produce a signal that, after suitable filtering, would have the same features (zero-crossings, peaks, etc.) correlated with the breathing period.

In some embodiments (which are described in more detail below), the values for the breathing related-feature can be compared to a quality criterion, and any value not meeting the quality criterion can be discarded. The quality criterion and its threshold value can depend on the breathing-related feature. For example, where the breathing-related feature is a candidate breathing period, the quality criterion can comprise a lower bound for the breathing period that corresponds to a maximum possible respiration rate for the subject, and any breathing period that is below the lower bound can be discarded and not used in the subsequent analysis. For example, the maximum respiration rate for a subject may be 160 respirations per minute (RPM), in which case a lower bound for the breathing period can be 0.375 seconds (=1/(160/minute)). Likewise, where the breathing-related feature is a candidate respiration rate, an upper bound can be specified of 160 RPM and any candidate respiration rate above this bound can be discarded.

Thus, in step 105, the values for the breathing-related feature determined in step 103 are used to form a histogram. As is known, a histogram is a function that counts the number of observations that fall into each of a number of disjoint categories (known as bins). In other words, the values for the breathing-related feature are grouped into a plurality of groups (bins) based on their values. Each group or bin relates to a specific value or specific range of possible values. The width of the bins (e.g. the range of values in each bin) can be set to any desired amount. However, bins that are too narrow may result in the bins having low numbers of values therein. The count associated with each group (bin) is the number of occurrences of a value or values for the breathing-related feature corresponding to the group.

Once the histogram has been determined, a weighted average center of the histogram is determined, and the respiration rate of the subject is determined as the respiration rate associated with the weighted average center. This step is described in more detail below and in connection with the preferred embodiment.

The weighted average center of the histogram is determined in step 107 by applying a weighting to one or more of the counts in the histogram to form weighted counts, and determining the mean of the histogram with the weighted counts. The weighted average center is thus the mean of the weighted histogram.

The weighting is applied to the counts such that the resulting mean of the histogram is weighted towards the value or values of the breathing-related feature for the group having the highest count. Put another way the weighting is applied such that the value or values of the breathing-related feature for the group or groups having the highest counts are emphasized (i.e. have more influence) in the mean of the histogram. This emphasizing of the peaks is particularly useful for determining the respiration rate for children, since their breath-to-breath intervals can vary significantly and thus several groups in the histogram may have high or relatively high count values.

As noted above, the histogram formed in step 105 has a count value for each group. The count value is any integer value equal to or greater than 0. Applying a weighting in step 107 results in the value of at least one of the count values being modified, and the mean of the histogram is determined using these modified (weighted) values. It should be noted that the term "weighted counts"/"weighted values" refers to all of the count values of the histogram after the weighting has been applied, regardless of whether a particular count value has been modified by the application of the weighting or not.

In general, the mean of a histogram is given by multiplying each histogram index (the parameter value associated with each group or bin) by the associated count value, taking the sum of these and dividing the sum by the total number of counts. Thus, the weighted average center of the histogram (the mean of the histogram with the weighted counts) is determined by applying a weighting to the count associated with one or more of the groups to form weighted counts, multiplying the histogram index (the parameter value associated with each group or bin) by the associated weighted count value, taking the sum of these and dividing the sum by the sum of the weighted counts.

In some embodiments, in order to provide weighting towards the bins having the highest number of values, non-linear compression is used on the number of values to emphasize higher numbers of values. For example the number of values in each bin, V, can be taken to the nth power (i.e. $V^n$), where n>1, and these results can be used in determining the average center of the histogram and thus the respiration rate. Thus, in some embodiments, applying a weighting to the count associated with one or more groups can comprise determining the weighted count for each group as the nth power of the respective count, where n is any number greater than 1. For example, for a histogram with count values of 4, 12, 1 and 9 for four groups and n=2, the weighted counts will be 16, 144, 1 and 81 respectively, which has the effect of emphasizing the two peaks in the mean of the histogram (which is formed using the weighted counts 16, 144, 1 and 81).

In some embodiments (that are described in more detail below), once the histogram has been formed (i.e. once all of the values of the breathing-related feature have been placed into a group/bin) in step 105, applying the weighting in step 107 can comprise discarding from the histogram any group having a count that is less than a threshold number. It will be appreciated that this is equivalent to setting the count to zero for any group where the count is less than the threshold number. Thus, any group in the histogram that has less than a threshold number of values in the group can be discarded or otherwise disregarded or considered empty (i.e. as having no values therein). This discarding means that the groups that have a larger number of values contribute more towards the respiration rate that is determined from the histogram. In the above example of a histogram with count values of 4, 12, 1 and 9 for four groups, and a threshold of 5, the weighted counts will be 0, 12, 0 and 9 respectively, which has the effect of emphasizing the two peaks in the mean of the histogram (which is formed using the weighted counts 0, 12, 0 and 9).

In some embodiments, applying the weighting in step 107 can comprise subtracting a threshold value from the respective count for each group. In the event that the threshold value is greater than a particular count value (i.e. the result of subtracting the threshold value from that count value is less than 0), the weighted count value for that count value is set to 0. The threshold value can be any fixed value (e.g. a predetermined value), or in some embodiments it can be calculated based on the count for the highest peak. For example, the threshold value can be calculated as a percentage (less than 100%) of the highest count. In one example the threshold value can be 20% of the highest count value. In the above example of a histogram with count values of 4, 12, 1 and 9 for four groups, and a threshold value of 50% of the highest count (so a threshold value of 6), the weighted counts will be 0, 6, 0 and 3 respectively, which has the effect of emphasizing the two peaks in the mean of the histogram (which is formed using the weighted counts 0, 6, 0 and 3).

In embodiments where each value of the breathing-related feature is a candidate breath period, the histogram will be formed from the candidate breath periods, and thus the weighted average center of the histogram (the mean of the histogram with the weighted counts) will provide an estimated breath period for the subject. This estimated breath period (measured in seconds) can then be converted to respiration rate (in breaths per minute).

The difference between the embodiment in which the breathing-related feature is a candidate breath period and the embodiment in which the breathing-related feature is a candidate respiration rate is that the scale of the histogram array indices is time based (t) or frequency based (1/t). Other embodiments are possible where the scale is logarithmic or uses another non-linear transformation (like taking a certain power or using a conversion table where the bin distances are derived from patient data). For most of these scales there will be an encoding step to translate the breath period durations to the chosen scale and a decoding step to translate the final result. The choice of scale changes the relative width amongst various bins. Reference data can be used to score each scale candidate and choose the best scale.

In embodiments where the sensor is an accelerometer that outputs an acceleration signal for each of the measurement axes, steps 103 and 105 can be performed for each signal and the histograms combined into a single histogram before performing step 107. When combining the histograms into a single histogram, the histograms can be given different weightings depending on a quality factor, such as, for example the signal energy. Alternatively, steps 103, 105 and 107 can be performed for each signal, and the respiration rates determined from the histograms can be averaged to provide the respiration rate for the subject. Again, the respiration rates determined from each histogram can be weighted when taking the average, with the weighting being based on, for example, a quality factor such as the signal energy.

Figure 3:
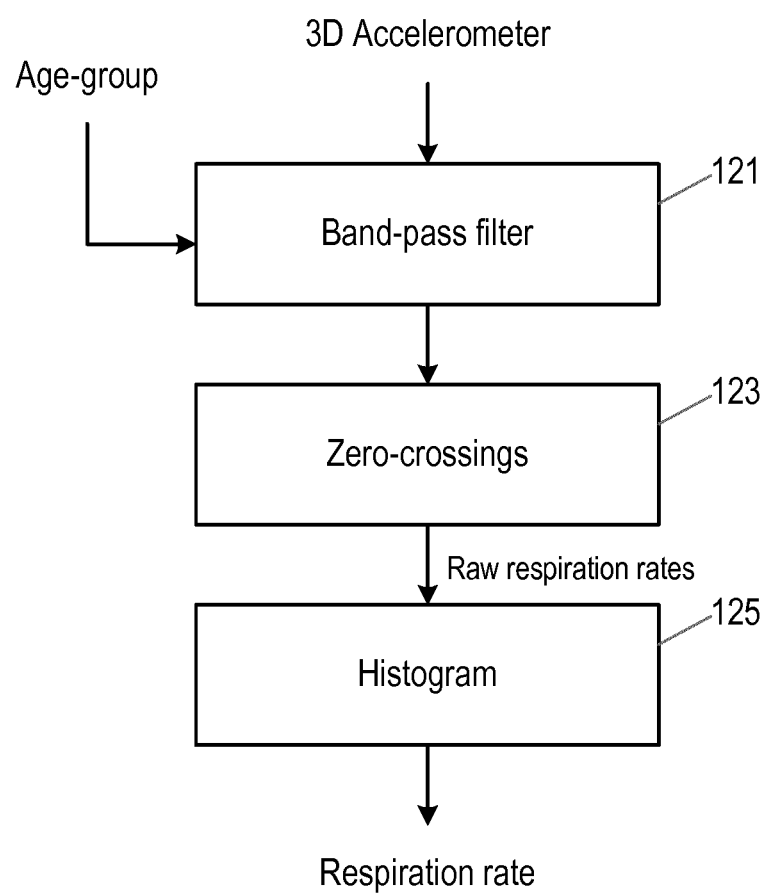
FIG. 3 is a flow chart illustrating an embodiment of the invention.

Various preferred embodiments of the invention are described in more detail below. In these preferred embodiments, as outlined by the flow chart in FIG. 3, the respiratory rate is determined using measurements from a 3D accelerometer (with X, Y and Z axes), the 3D accelerometer signal is band-pass filtered (step 121) to remove frequencies outside a valid respiration range (which can be specific to a particular age group of subjects), the breathing-related feature is a candidate breath period which is given by the time between zero-crossings of the same trend (either positive or negative) of the acceleration signal (step 123), each candidate breath period is converted into a candidate respiration rate (also referred to below as a 'raw respiration rate'), which is thereafter used to generate a histogram by counting how often each raw respiration rate is encountered, weighted by their durations (step 125). Then, from this histogram, the respiration rate is calculated as the weighted mean center of the histogram (i.e. by applying a weighting to the count associated with one or more of the groups to form weighted counts and determining the respiration rate from a mean of the histogram with the weighted counts).

It will be appreciated by those skilled in the art that various ones of the embodiments below are not limited to use with a 3D accelerometer signal and they can be applied to signals from other types of sensors. In addition, those skilled in the art will appreciate that various ones of the embodiments below are not limited to the breathing-related feature being a candidate breath period as defined above, and they can be applied to a candidate breath period that is determined in a different way (i.e. other than using the zero-crossings) and/or applied to other types of breathing-related feature.

As indicated above, the accelerometer 6 has three measurement axes: X, Y and Z. The main contribution to the measured acceleration will be that of gravity, with the contribution of gravity to each of these axes depending on the orientation of the accelerometer 6. When the orientation of the accelerometer 6 is changed, the contribution of gravity to each of the measurement axes will change accordingly.

When the accelerometer 6 (or more generally the apparatus 2 when the accelerometer 6 is part of the apparatus 2) is placed on the belly of a subject, particularly a child, the accelerometer 6 will move slightly with each breath. This movement is generally too small to have a significant contribution to the acceleration (at least compared to the acceleration due to gravity present in the signal). However, the orientation of the sensor 6 does change slightly with each breath, and it is this change in orientation that can be used to measure the breathing/respiration rate.

The breathing motion produces a (more-or-less) sinusoidal frequency component on one or more axes of the accelerometer 6. Signal components that are not related to the breathing need to be filtered out. One of these components is the constant part of the gravity vector. In addition, components produced by non-breathing motions like the motion of the hands and the feet, interventions by the caregivers, posture changes, etc. need to be filtered out (as much as possible).

Figure 4:
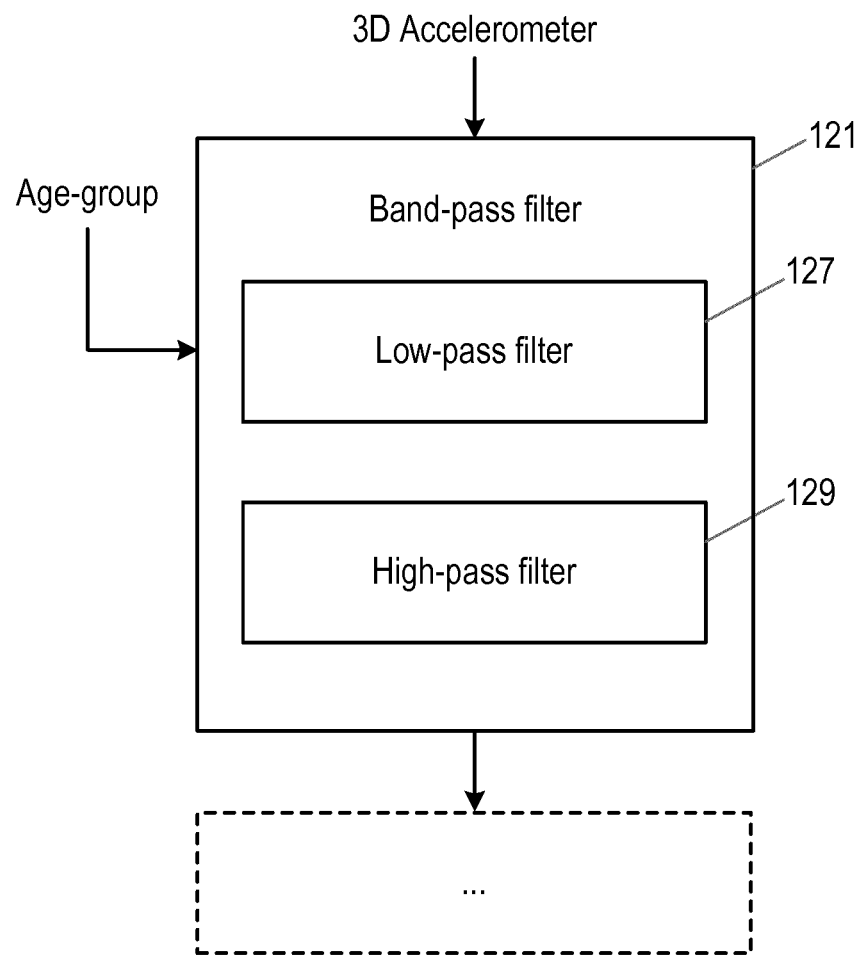
FIG. 4 illustrates an exemplary band-pass filter.

This filtering can be done in step 121 using a band-pass filter. In some embodiments the band-pass filter is implemented as a single filtering stage. However, as shown in FIG. 4, the band-pass filter can be implemented as a low-pass filter 127 followed by a high-pass filter 129 (although it will be appreciated that the filters can be used in the opposite order). In some embodiments the band-pass filter is a cascade or series of two $2^{nd}$ order infinite impulse response (IIR) filters. In some embodiments the cut-off frequencies of these filters can be set based on the age of the subject.

For example, the younger the subject (and particularly the younger the child), the higher the expected range of the respiration rate. Table 1 below shows the normal respiration rates for children of different age groups, with the upper limits being defined by the World Health Organization (WHO) as the threshold for classifying a breath measurement as fast breathing. In this example, the lower limit for normal breathing is given as half of the upper limit.

TABLE 1

| Age group | Age | Respiration Rate per Minute |
| --- | --- | --- |
| 1 | 0-2 Months | 30-60 |
| 2 | 2-12 Months | 25-50 |
| 3 | 1-5 Years | 20-40 |

The high-pass filter is primarily provided in order to remove the gravity component in the acceleration signal. In some embodiments, the high-pass filter 129 can be a second order Bessel filter. In some embodiments, the high-pass filter 129 can be used with cut-off frequency that is set at 5 RPM (Respirations per minute) below the lower limit of the normal respiration rate given in Table 1. Thus, for age groups 1, 2 and 3 the cut-off frequency is set at respectively 25, 20 and 15 RPM. It will be appreciated by those skilled in the art that 5 RPM below the lower limits given in Table 1 is merely an exemplary way to determine a cut-off frequency, and the cut-off frequency can be determined in other ways and/or with different values above or below the lower limit.

In some embodiments, a relationship between the cut-off frequency f h and the age group A can be given by:

$$f_h = 30 - 5A \quad (1)$$

Figure 5:
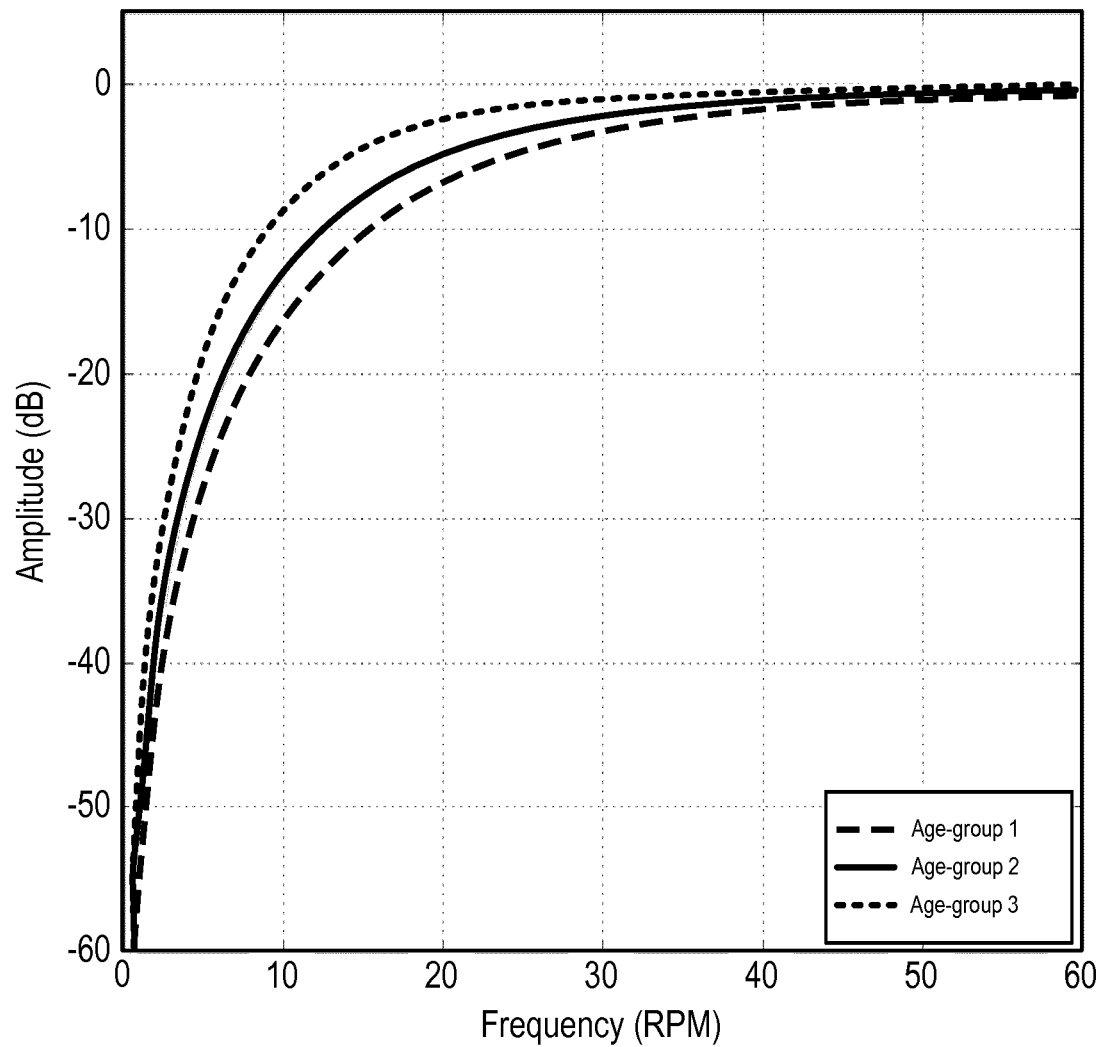
FIG. 5 is a graph illustrating high-pass filter spectra for different age groups.

This linear relationship is inspired by the upper and lower respiration limits that also have a linear relationship with the age group. The graph in FIG. 5 shows the high-pass filter spectra for each of the age groups in Table 1. It should be noted that in FIG. 5 the frequency axis is multiplied by 60 to show respirations per minute (RPM) instead of Hertz, Hz (cycles per second).

The filtering operation can be done using:

$$y[n] = (b_0 x[n] + b_1 x[n-1] + b_2 x[n-2] a_1 y[n-1] - a_2 y[n-2])/a_0 \quad (2)$$

where x is the array with the input samples, y the filtered output samples and n the current array index (bin). Table 2 below shows exemplary values for the filter coefficients.

TABLE 2

| Age group | $a_0$ | $a_1$ | $a_2$ | $b_0$ | $b_1$ | $b_2$ |
|---|---|---|---|---|---|---|
| 1 | 1.0 | −1.95500 | 0.95567 | 0.97767 | −1.95533 | 0.97767 |
| 2 | 1.0 | −1.96394 | 0.96437 | 0.98208 | −1.96416 | 0.98208 |
| 3 | 1.0 | −1.97292 | 0.97316 | 0.98652 | −1.97304 | 0.98652 |

In some embodiments the low-pass filter 127 is a $2^{nd}$ order Butterworth filter. In some embodiments, the cut-off frequency can be set according to:

$$f_l = 170 - 30A \quad (3)$$

where A is the age group. So for age groups 1, 2 and 3 the cut-off frequency is set at respectively 140, 110 and 80 RPM.

Figure 6:
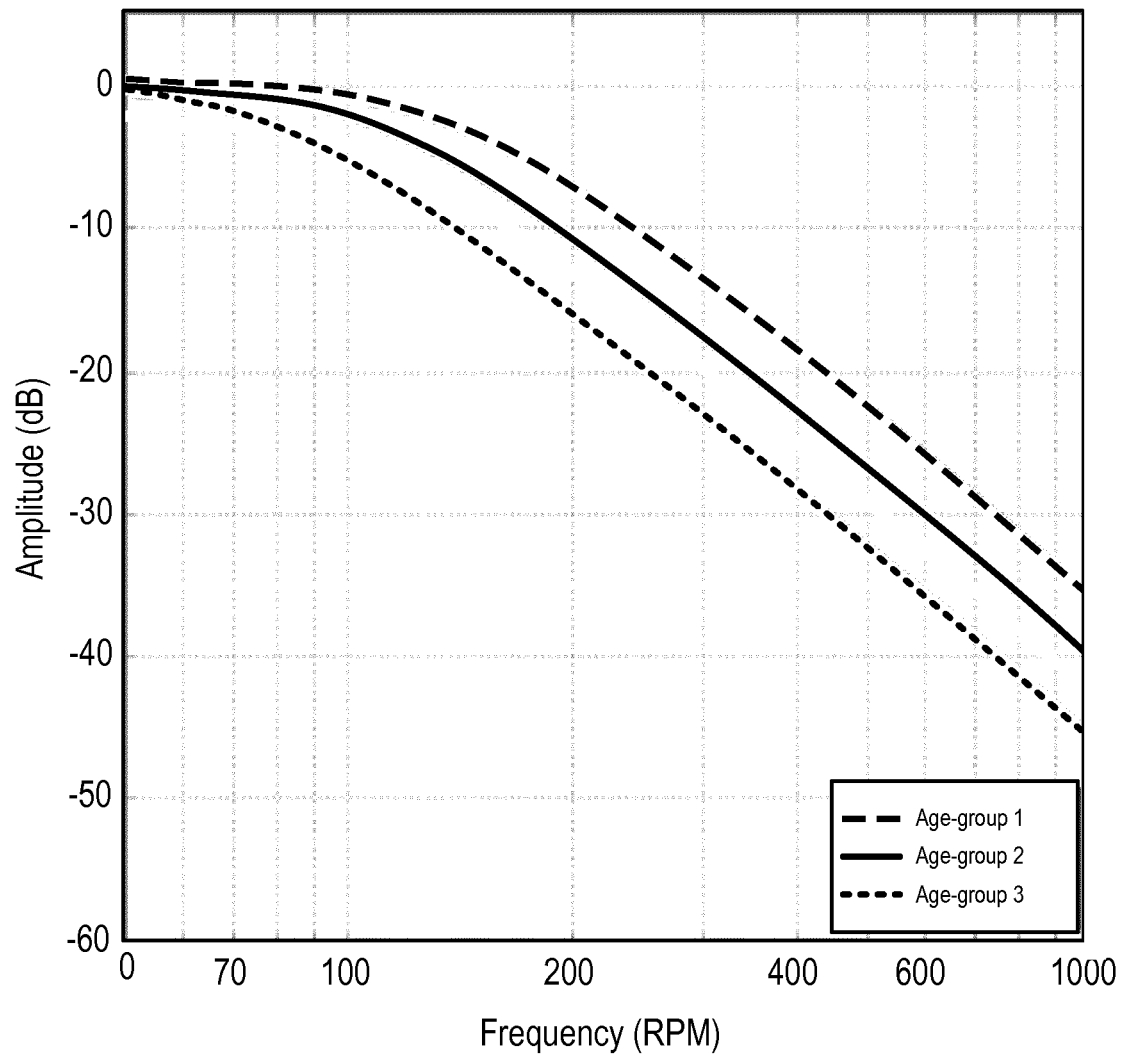
FIG. 6 is a graph illustrating low-pass filter spectra for different age groups.

The graph in FIG. 6 shows the magnitude spectrum of the low-pass filters for each of the age groups in Table 1. As with FIG. 5, it should be noted that in FIG. 6 the frequency axis is multiplied by 60 to show RPM instead of Hz. Table 3 below shows exemplary values for the filter coefficients that can be used in the filtering operation shown in equation (2).

TABLE 3

| Age group | $a_0$ | $a_1$ | $a_2$ | $b_0$ | $b_1$ | $b_2$ |
|---|---|---|---|---|---|---|
| 1 | 1.0 | −1.79330 | 0.81275 | $4.8616e^{-3}$ | $9.7233e^{-3}$ | $4.8616e^{-3}$ |
| 2 | 1.0 | −1.83741 | 0.84967 | $3.0646e^{-3}$ | $6.1291e^{-3}$ | $3.0646e^{-3}$ |
| 3 | 1.0 | −1.88165 | 0.88827 | $1.6556e^{-3}$ | $3.3112e^{-3}$ | $1.6556e^{-3}$ |

As noted above, in step 123, values for candidate breath periods are determined based on zero-crossings in the accelerometer signal. Ideally, the band-pass filtered accelerometer signal will pass the zero line twice with each breath, once when the signal changes sign and becomes positive (referred to as a positive zero-crossing) and once when the sign becomes negative (referred to as a negative zero-crossing). The time or distance between two (consecutive) positive zero-crossings or between two (consecutive) negative zero-crossings is called a candidate breath period. In practice noise and motion artefacts will introduce extra zero-crossings that will distort the values of some candidate breath periods.

There is no direct relationship between an inhalation or an exhalation and the sign of a zero-crossing. That mostly depends on the position and orientation of the accelerometer 6. Moreover, the invention is not concerned with whether the partial breath motion belongs to an inhalation or an exhalation. Even though there can be a clear difference between the two for an adult (where the inhalation is usually faster than an exhalation), the distinction is not that clear for small children, and the breathing motion looks more like a sinusoid. Since the invention is concerned with identifying the respiratory rate in children as well as adults, the invention does not make use of the difference between the duration of inhalations and exhalations to identify the respiration rate.

Figure 7:
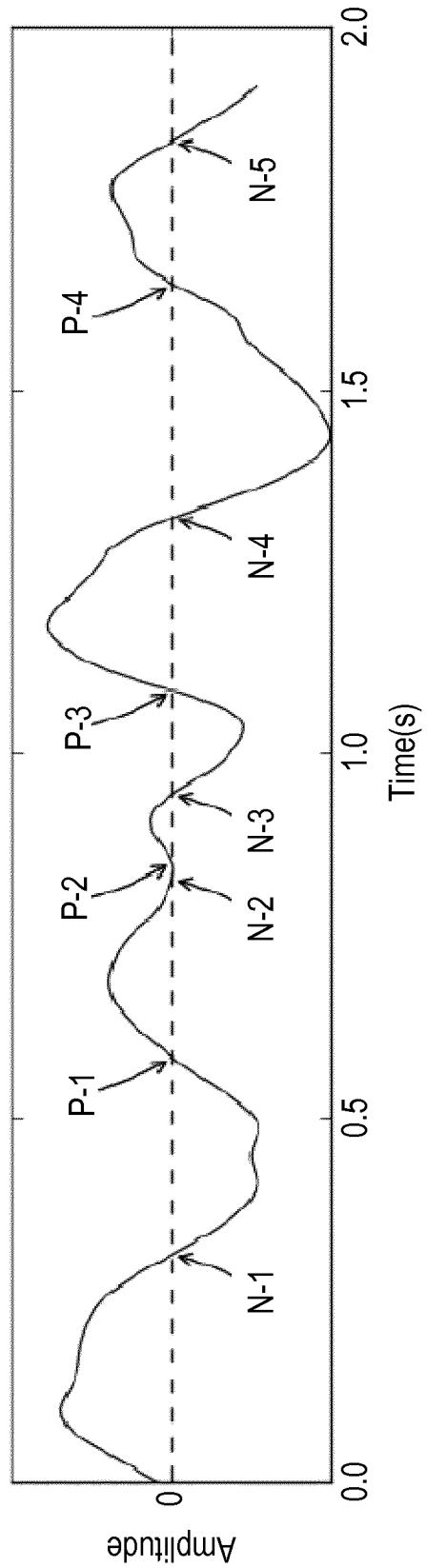
FIG. 7 shows the zero-crossings in an exemplary band-pass filtered acceleration signal.

An exemplary band-pass filtered accelerometer signal for one of the measurement axes of the accelerometer 6 is shown in FIG. 7, and the positive zero-crossings have been labelled P-1 to P-4 and the negative zero-crossings have been labelled N-1 to N-4. As noted above, the distance between consecutive positive zero-crossings (e.g. between P-1 and P-2, P-2 and P-3, etc.) and consecutive negative zero-crossings (e.g. between N-1 and N-2, N-2 and N-3, etc.) form the candidate breath periods. Each candidate breath period can be converted into a candidate respiration rate (also called 'raw respiration rate') using:

$$r = 60/d \quad (4)$$

where r is the respiration rate and d the duration of the breath period in seconds. Table 4 below shows candidate breath periods obtained from the signal in FIG. 7 and the corresponding candidate respiration rates.

TABLE 4

| Periods | Duration(s) | RPM |
|---|---|---|
| N-1 → N-2 | 0.52 | 116 |
| P-1 → P-2 | 0.27 | 224 |
| N-2 → N-3 | 0.12 | 514 |
| P-2 → P-3 | 0.24 | 254 |
| N-3 → N-4 | 0.38 | 158 |
| P-3 → P-4 | 0.56 | 107 |
| N-4 → N-5 | 0.52 | 116 |

For a perfectly constant breathing motion, the duration of a single breath period would be enough to calculate the respiration rate. If all of the candidate breath periods referred to actual breaths (i.e. if there was no noise or motion artefacts in the acceleration signal that cause additional zero-crossings), then the mean respiration rate would be given by:

$$r_{mean} = \frac{60N}{\sum_{i=0}^{N-1} d_i} \quad (5)$$

where N is the number of breath periods and $d_i$ the candidate breath durations.

Equation (6) below calculates the mean respiration rate by weighting the raw respiration rates $r_i$ by their durations $d_i$:

$$r_{mean} = \frac{\sum_{i=0}^{N-1} d_i r_i}{\sum_{i=0}^{N-1} d_i} \quad (6)$$

As noted above, calculating the mean respiration rate from the raw respiration rates would only work for very clean acceleration signals that do not include noise or motion artefacts. However, in practice there will be noise and a certain level of non-breathing motion. The candidate breathing periods that are affected by these artefacts need to be filtered out.

In order to do this, it is recognized that breathing is more or less periodic, and even though successive breathing periods might have significantly different durations, overall, the periods will be concentrated around the mean respiration rate. By using a histogram of raw respiration rates, it is possible to emphasize this concentration and filter out the rest. Thus, as noted above in step 105 of FIG. 2 and step 125 of FIG. 3, a histogram H is formed by counting how often each raw respiration rate $r_i$ is encountered, weighted by their durations $d_i$:

$$H_{r|0 < r \leq M} = \sum_{i=0}^{N-1} \begin{cases} d_i & \text{if } r - 0.5 \leq r_i \leq r + 0.5 \\ 0, & \text{otherwise} \end{cases} \quad (7)$$

The histogram has a fixed size. The maximum respiration rate M is age-group dependent and can be one of 170, 160 or 150 RPM for respectively age-groups 1, 2, and 3. In some embodiments, candidate respiration rates above this limit can simply be discarded. This limit is chosen to be well above the fast-breathing threshold of the age group (+110 RPM). It will be appreciated that the maximum value will be different for subjects in other age groups.

Figure 8:
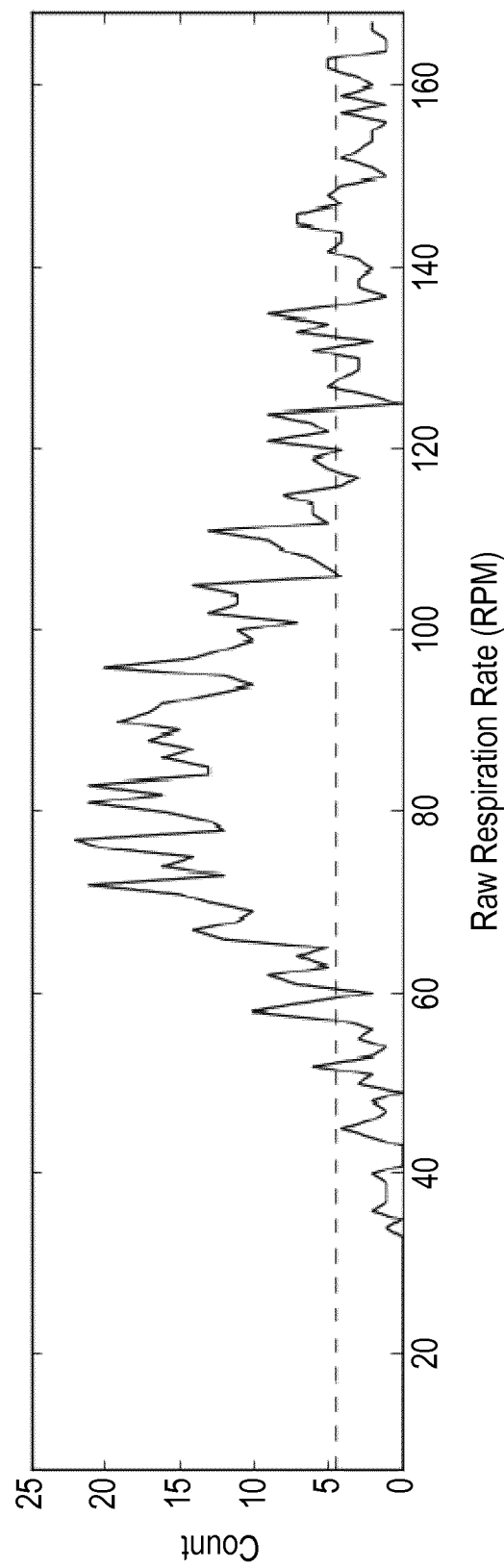
FIG. 8 shows an exemplary histogram.

The graph in FIG. 8 shows a histogram of a respiration measurement.

In some embodiments, to emphasize respiration rates that occur more often than others (and which are assumed therefore to more likely correspond to actual respiration rates rather than artefacts), a certain threshold value $t_h$ is subtracted from the number of values in each bin of the histogram. Any bin that has a negative value following this subtraction are set to 0:

$$H'_{r|0 < r \leq M} = \begin{cases} H_r - t_h & \text{if } H_r > t_h \\ 0, & \text{otherwise} \end{cases} \quad (8)$$

The threshold value $t_h$ can be set to a certain percentage (e.g. 20%) of the highest number of values in the bins of the histogram. The dashed line in FIG. 8 illustrates a threshold value that can be used to suppress some of the bins having a small number of candidate respiration values therein.

Finally, the respiration rate is calculated as the weighted mean center of the histogram:

$$r_{mean} = \frac{\sum_{r=0}^{M} H'_r r}{\sum_{r=0}^{M} H'_r} \quad (9)$$

The above description indicates various exemplary and preferred embodiments for determining the respiration rate according to the invention. The following description sets out various improvements that can be made to the above exemplary and preferred embodiments, and it should be appreciated that any one or more of these improvements can be used individually or in combination to improve the basic method shown in FIGS. 2 and 3. Where the improvements are described in terms of a particular embodiment, e.g. an acceleration signal, identifying zero-crossings and/or forming the histogram from candidate respiration rates, those skilled in the art will appreciate that those improvements can also be applied to embodiments in which another type of sensor is used and/or another type of breathing-related feature is determined from the measurement signal.

Resampling

The first improvement relates to the resampling of the signal from the sensor 6. Although some sensors, for example accelerometers, can be set to operate at a certain sampling frequency, e.g. 100 Hz, the true sampling frequency can be significantly different (e.g. there can be a deviation of ±10%). Therefore it can be desirable to resample the measurement signal to the required sampling frequency before any processing is carried out on the signal. Those skilled in the art will be aware of various ways in which a measurement signal can be resampled to a desired frequency and no further details are provided herein.

Skipping an Initial Signal

It has been noted that the resampling (if required) and the band-pass filtering stage introduce a certain delay into the filtered signal and the filters need some time to settle. In addition the high-pass filter 129 needs to remove the strong component of the Earth's gravitational pull. This means that the initial zero-crossings are less reliable. Therefore, an initial portion of the measurement signal after the respiration rate processing is initiated can be discarded or skipped (i.e. no further processing is done to calculate breath periods). For example the first two seconds of the measurement signal can be skipped.

In addition, the apparatus 2 may be activated by pressing a button the apparatus 2 which may cause the apparatus 2 to move or shake, and therefore skipping or discarding the first few seconds of the measurement signal ensures that these artefacts do not influence the measured respiration rate.

Signal Level

As noted above, in an ideal measurement situation the subject (e.g. a child) stays calm and generally motionless during the measurement and the only significant movement that the accelerometer records is that of the breathing. In most cases, however, there will be some motion due to movement of the legs and feet, coughing, interventions by the caregivers, etc. During motion, the signal level of the band-pass filtered accelerometer signal is usually much higher than during breathing. Therefore in some embodiments, further processing of the signal is skipped if the signal level is above a certain threshold, which improves the robustness of the method to motion artefacts.

The threshold used to determine if the signal is too high can be set to any desired level. For example it can be set at a certain percentage of gravitational acceleration (e.g. 13.33% of the 1 g level (the default force that the accelerometer will measure due to gravity)). For example for an accelerometer 6 that is set to operate at ±2 g where the samples are stored as 16-bit signed integer values, the 1 g level will be 16384.

Therefore in some embodiments the absolute signal level of the high-pass filtered signal (i.e. the output of step 121) is compared to the threshold within a half period (i.e. between two zero-crossings). If any of the last three half-periods is above the threshold, further processing of that part of the signal is skipped. The reason for taking an extra half period is to compensate for the time-smearing due to filtering.

Breath Level

If the apparatus 2 or sensor 6 is not worn tightly enough on the subject (i.e. it is too loose), the signal level will be too low (i.e. the motions due to breathing will not be clearly represented in the signal, and so this can be identified and further processing of the signal skipped. If the apparatus 2 is not placed correctly on the subject, or, for example, if the measurement process is started while the apparatus 2 is lying on a table, the apparatus 2 should not output a respiration rate.

To implement this low signal level detection, a so-called 'breath level' can be measured. The breath level is defined as the signal level during one breath period, and it can be calculated as the relative area of the band-pass filtered accelerometer signal between three zero-crossings:

$$l_p = \frac{\sum_{i=z[p]}^{z[P+2]} |s[i]|}{z[p+2] - z[p]} \quad (10)$$

where $l_p$ is the breath level of the period with index p, and z is the zero-cross indexes into the accelerometer signal s of a certain axis.

The threshold for detecting a signal that is too low can be set to any desired value. For example it can be set in a similar way to the threshold for detecting if the signal level is too high (i.e. as a certain percentage of gravitational acceleration). For example the threshold can be set at 0.18% of the 1 g level.

In some embodiments this threshold can be set to a higher value (e.g. 0.52% of the 1 g level) for breath periods with a duration that is significantly different (e.g. more than 17% different) from the previous breath duration. This can help to prevent the skipping of weak but regular breathing motions.

Breath Quality

In some embodiments, the breath level as determined above can also be used as a quality measure, with the higher the breath level, the stronger (and more stable) the breathing signal is. The following exemplary equation can be used for calculating the breath quality as a percentage:

$$q = \frac{l(100 + 59d)}{0.021g} \quad (11)$$

where l is the breath level of the period, d the period duration, g the 1 g scale and q the breath quality.

If the breath quality is above 100%, a further check (e.g. as described above) may need to be done to see if the excessive breath level is due to a motion artefact. If q is above 100% and the breath duration is significantly different (e.g. by more than 17%) from the previous breath duration, this period can be classified as a motion-artefact period and further processing of this part of the signal can be skipped. If not, and the breath quality is above 100, it is limited to 100. I.e.

$$q' = \min\{100, q\} \quad (12)$$

Figure 9:
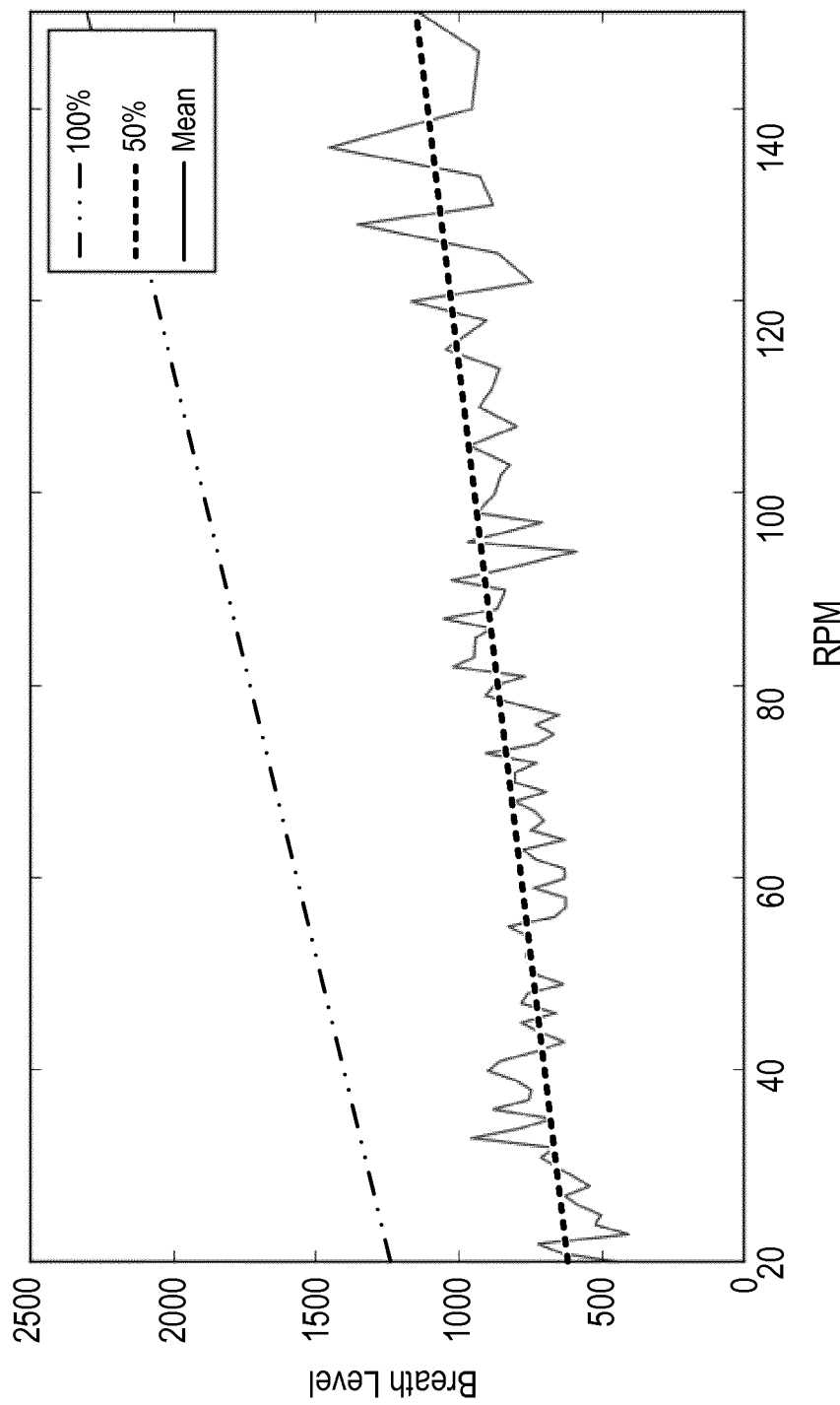
FIG. 9 is a graph illustrating the mean breath levels of a sample of children.

The graph in FIG. 9 shows the relationship between the breath level and the breath quality. The 'Mean' line is the mean breath level that was calculated by analyzing clinical data of 29 children aged between 0 and 5 years. The 50% and 100% lines show the corresponding breath quality. It can be seen that with increasing breathing rate, the breathing motion produces larger angular changes in the 3D gravity vector of the accelerometer.

Breath Quality as Weight

In some embodiments, the breath quality can be used as a weight with which the raw respiration values are counted. This way, strong breaths have more influence on the final result (i.e. the final respiration rate) than weak breaths. Thus, equation (7) can be modified to:

$$H_{r|0 < r \leq M} = \sum_{i=0}^{N-1} \begin{cases} d_i q_i' & \text{if } r - 0.5 \leq r_i \leq r + 0.5 \\ 0, & \text{otherwise} \end{cases} \quad (13)$$

where H is the histogram array, $r_i$ is the respiration value with index i, r is the index into the histogram ($r_i$ rounded to an integer number) and $q_{i'}$ is the breath quality.

Reduced Histogram Size

In some embodiments, the histogram size can be the same as the valid respiration range. For example histogram size M can be one of 170, 160 or 150 RPM for age-groups 1, 2, and 3 respectively. However, in some embodiments the histogram size can be reduced by linearly downscaling the raw respiration values by a certain amount before counting and upscaling the end result by the same amount. This enables neighboring respiration rate values to be combined into the same peak in the histogram and makes the algorithm more robust to jitter in the respiration values. An exemplary scale factor that can be used is 0.125.

In some embodiments, to avoid quantization error due to scaling, each raw respiration rate can be distributed over two neighboring histogram indices. The equations for performing these operations are:

$$i = \left\lfloor \frac{r}{8} \right\rfloor \quad (14)$$

$$w = 1 - \left(\frac{r}{8} - i\right) \quad (15)$$

$$H[i] = H[i] + wq \quad (16)$$

$$H[i+1] = H[i+1] + (1-w)q \quad (17)$$

$$M' = \text{round}\left(\frac{M}{8}\right) \quad (18)$$

$$H'_{i|0 < i \leq M'} = \begin{cases} H_i - t_h & \text{if } H_i > t_h \\ 0, & \text{otherwise} \end{cases} \quad (19)$$

$$\text{rate} = 8 \frac{\sum_{i=0}^{M'} i H'_i}{\sum_{i=0}^{M'} H'_i} \quad (20)$$

where the operator ⌊ ⌋ removes the fractional part of the scaled raw respiration value r, i and i+1 are the two indices into the histogram H for increasing the count, and w and (1−w) are the weights with which the count is increased. The histogram size is also reduced to M'. M' for age groups 1, 2, and 3 is respectively 21, 20 and 19.

Skipping the Threshold for Highly Periodic Breathing

When the breathing is highly periodic, the resulting histogram will have a dominant peak. This peak is usually spread over two neighboring indices (see the above improvement). Subtracting the threshold $t_h$ will shift the center of the area from which the mean respiration rate is calculated, unless the area below the threshold is perfectly symmetric. For a narrow peak this shift will affect the final accuracy of the measurement. Therefore, in some embodiments, these special cases can be detected and the weighted mean center can be calculated without subtracting a threshold.

In some embodiments, a dominant narrow peak can be detected by examining the difference between the first index (bin) and the last index (bin) that is above the threshold. If this difference is below 2 indices (bins), the final respiration rate is calculated without subtracting a threshold. The area for calculating the respiration rate can be the area above the threshold line including one extra sample at the boundaries to also take into account the side lobes of the peak that is masked by the threshold.

With this improvement, equation (20) becomes:

$$B = \underset{i}{\operatorname{argmin}}\left(H_i > t_h\right) \quad (21)$$

$$E = \underset{i}{\operatorname{argmax}}\left(H_i > t_h\right) \quad (22)$$

$$B' = \begin{cases} B-1 & \text{if } B > 1 \\ 0 & \text{, otherwise} \end{cases} \quad (23)$$

$$\text{rate} = 8 \begin{cases} \dfrac{\sum_{i=B'}^{E+2} iH_i}{\sum_{i=B'}^{E+2} H_i}, & \text{if } E - B < 2 \text{ and } E + 1 < M' \\ 0, & \text{if } E - B < 2 \text{ and } E + 1 = M' \\ \dfrac{\sum_{i=0}^{M'} iH'_i}{\sum_{i=0}^{M'} H'_i}, & \text{otherwise} \end{cases} \quad (24)$$

where B is the first index (bin) into the histogram H that is above the threshold $t_h$ and E is the last index above the threshold $t_h$. The rate is calculated from the area between B and E, including one extra sample at the area boundaries. This is done by subtracting 1 from B and adding 1 to E. B should remain positive so equation (23) is used to get the clamped value B'. On the other hand if adding 1 to E makes the index go outside the array boundary M', the rate calculation is skipped (i.e. it is set to 0). This happens when the dominant peak is clipped by the histogram size. The resulting rate would be unreliable as the center of the area of the actual peak could be well above the valid respiration range.

Per Axis Histogram

Another improvement, which has been outlined above, is to calculate a histogram for each measurement axis separately and then combine them into one histogram, emphasizing the strongest axis.

If the breathing movement is mainly concentrated on one of the axes (e.g. X, Y or Z), the remaining axes will have lower energy and will be more affected by noise and other movements. The raw respiration rates from the stronger axis will show a better correlation with the actual breathing rate than the others.

To find the axis strength an energy measure is calculated:

$$E_{a \in \{x,y,z\}} = \sum_{i=0}^{M'} H_a[i]^2 \quad (25)$$

where $E_a$ is the energy for the axis a and $H_a$ is the histogram of that axis. The final (combined) histogram is then the sum of weighted histograms per axis:

$$H[i] = \dfrac{\sum\limits_{a \in \{x,y,z\}} E_a h_a[i]}{\max\limits_{a \in \{x,y,z\}} E_a}, \; 0 \le i < M' \quad (26)$$

Variable Measurement Duration

The WHO recommends a respiration rate measurement with a duration of 60 seconds, assuming the subject is calm during the measurement. Since not all breath periods will be collected or detectable in the sensor signal (e.g. because too strong and too weak periods are skipped), there is a need to check if enough candidate breath periods/candidate respiration rates have been collected in order to determine a respiration rate. In the case of candidate breath periods, if the total duration of valid breath periods is below a certain threshold, then the final respiration rate calculation can be skipped, or delayed until further breath periods have been identified. The total duration of valid breath periods is given by:

$$d_{sum} = \max_{a \in \{x,y,z\}} \dfrac{\sum\limits_{i=0}^{L_a} d_{a,i}}{2} \quad (27)$$

where a is the current axis, $L_a$ is the total number of valid breath periods of that axis and $d_{a,i}$ are the breath durations.

As both the positive and negative zero-crossings are counted, at every time instance there are two breath periods. That is why the summed candidate duration of an axis is divided by 2. The axis with the longest duration of valid periods is the final duration that is used.

In one example (where the intention is to obtain nearly one minutes' worth of measurements), the threshold for "enough data" can be set at 48 seconds ($d_{sum} \ge 48$). As soon as this amount is reached and the measurement is done in total for at least 60 seconds, further recording of accelerometer data can be stopped and a final respiration rate measurement is determined using the generated histograms. It will be appreciated that it may take some time to accrue enough data to meet the threshold, and as such the actual duration of a measurement can be much longer than 60 seconds. In some embodiments a maximum measurement time may be specified, after which a measurement signal is no longer obtained by the sensor 6. This may be used, for example, to conserve battery power in an apparatus 2 that may need to be used to obtain respiration rate measurements over a long period of time (e.g. over several days).

In some embodiments, the apparatus 2 can be used to continuously monitor the subject and provide a real-time respiration rate measurement (for example while a subject is exercising). In this case, measurements can be obtained continuously, and a respiration rate calculated and updated based on the most recently received set of measurement signals.

Figure 10:
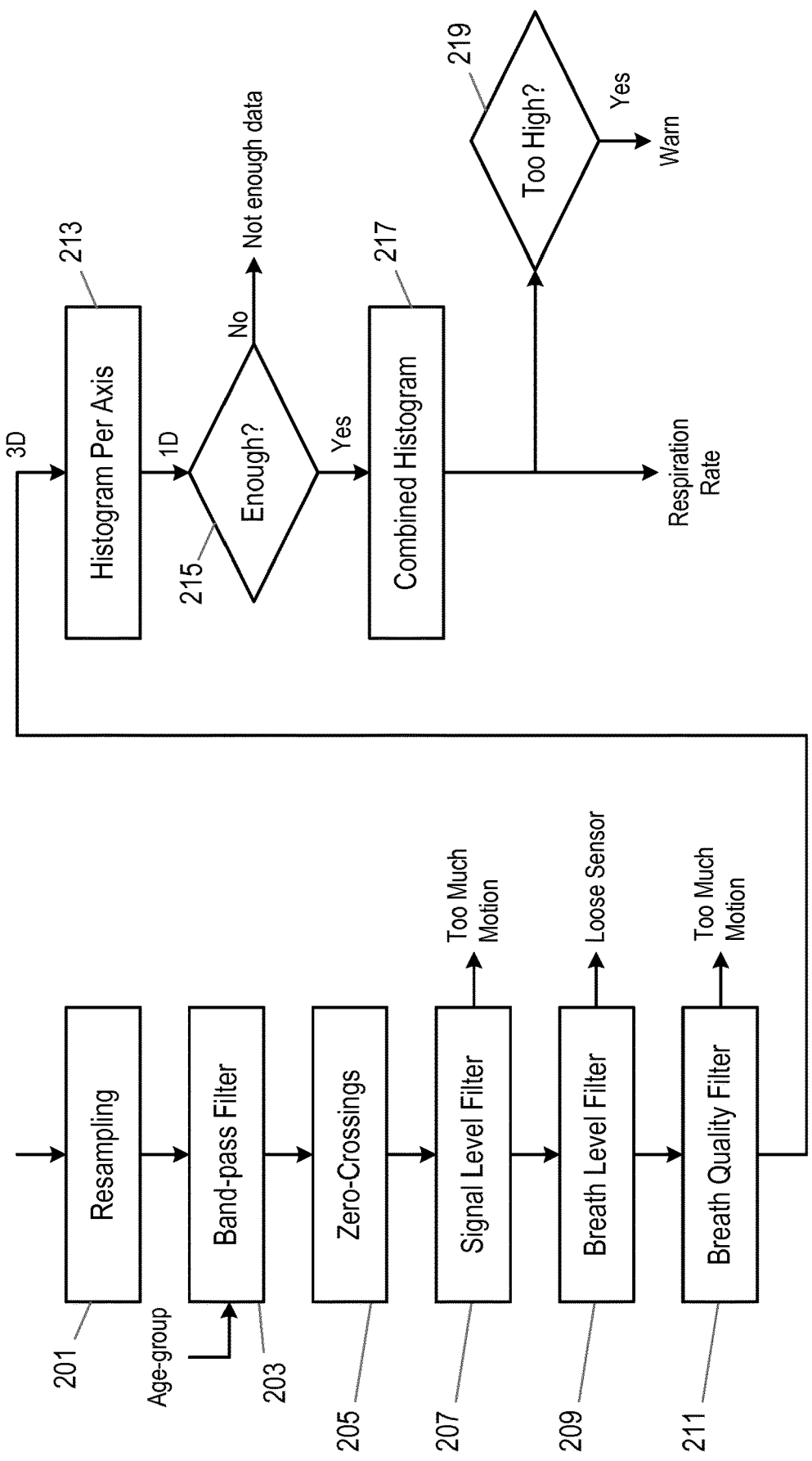
FIG. 10 is a flow chart illustrating a method according to a preferred embodiment of the invention.

The flow chart in FIG. 10 illustrates a method of determining a respiration rate measurement according to an exemplary embodiment in which various ones of the above improvements are implemented.

Thus, a 3D accelerometer signal is obtained, and in a first step, step 201, the signal is resampled to a desired sampling rate, for example 100 Hz. The resampled signal is then band-pass filtered (step 203), with the cut-off frequencies for the high- and low-pass filters being determined according to the age of the subject. The band-pass filtered signals are then analyzed to identify the zero-crossings (step 205). Candidate respiration rates are then determined from the distance between consecutive zero-crossings. A signal level filter is then applied to the candidate respiration rates (step 207) to remove candidates that are due to excessive motion. If this filter removes a substantial portion of the candidate respiration rates, an error or warning can be output by the apparatus 2 to indicate that there is too much motion of the apparatus 2 and/or of the subject. Assuming that the level of motion is adequately low, a breath level filter is applied (step 209) in order to determine if breaths can be detected in the signal. If an insufficient number of breaths can be detected, the apparatus 2 can output an error or warning indicating that the apparatus 2 may be too loose on the subject. Next, a breath quality filter (step 211) can be applied to again determine if there is too much motion. A histogram is then formed for each measurement axis (step 213). In the next step (step 215) it is determined whether enough data has been collected in order to determine a respiration rate. If enough data has been collected, the per-axis histogram are combined and the respiration rate determined (step 217). Optionally, the determined respiration rate can be compared to a threshold value to determine if the subject is breathing too rapidly (step 219), and if so, a warning or alarm can be output by the apparatus 2.

There is therefore provided an improved method and apparatus for determining a respiration rate of a subject, particularly a child.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining the respiration rate of a subject, the method comprising:
    obtaining a signal from a sensor that is worn or carried by the subject;
    analyzing the signal to determine a plurality of values for a breathing-related feature;
    forming a histogram from the plurality of values for the breathing-related feature, the histogram comprising a plurality of groups, each group corresponding to one or more possible values of the breathing-related feature, with each group having an associated count that corresponds to the number of occurrences of a value or values for the breathing-related feature corresponding to the group;
    applying a weighting to the count associated with one or more of the groups to form weighted counts by determining the weighted count for each group by subtracting a threshold value from a respective count wherein weighted counts are set to zero in the event that the threshold value is equal to or greater than the respective count; and
    determining the respiration rate from a mean of the histogram with the weighted counts.

2. A method as claimed in claim 1, wherein the step of determining the respiration rate from the mean of the histogram comprises determining the mean of the histogram by:
    (i) for each group, multiplying a value for the breathing-related feature corresponding to the group by the weighted count for the group;
    (ii) summing the result of (i) for each group;
    (iii) dividing the result of (ii) by the sum of the weighted counts.

3. A method as claimed in claim 1, wherein the step of applying a weighting to the count associated with one or more groups comprises:
    applying a weighting such that the mean of the histogram is weighted towards the value or values of the breathing-related feature for the group having the highest count.

4. A method as claimed in claim 1, wherein the step of applying a weighting to the count associated with one or more groups comprises:
    applying a weighting such that the value or values of the breathing-related feature for the group or groups having the highest counts are emphasized in the mean of the histogram.

5. A method as claimed in claim 1, wherein the step of applying a weighting to the count associated with one or more groups comprises:
    discarding from the histogram any group having a count that is less than a threshold number.

6. A method as claimed in claim 1, wherein the step of applying a weighting to the count associated with one or more groups comprises:
    determining the weighted count for each group as the nth power of the respective count, where n is any number greater than 1.

7. A non-transitory computer readable medium computer comprising a computer readable code embodied therein, the computer readable code being configured such that, on execution by a suitable computer or processor, the computer or processor is caused to:
    obtain a signal from a sensor that is worn or carried by the subject;
    analyze the signal to determine a plurality of values for a breathing-related feature;
    form a histogram from the plurality of values for the breathing-related feature, the histogram comprising a plurality of groups, each group corresponding to one or more possible values of the breathing-related feature, with each group having an associated count that corresponds to the number of occurrences of a value or values for the breathing-related feature corresponding to the group;
    apply a weighting to the count associated with one or more of the groups to form weighted counts by determining the weighted count for each group by subtracting a threshold value from a respective count; wherein weighted counts are set to zero in the event that the threshold value is equal to or greater than the respective count; and
    determine the respiration rate from a mean of the histogram with the weighted counts.

8. An apparatus for determining the respiration rate of a subject, the apparatus comprising:
a processing unit configured to:
receive a signal from a sensor;
analyze the signal to determine a plurality of values for a breathing-related feature;
form a histogram from the plurality of values for the breathing-related feature, the histogram comprising a plurality of groups, each group corresponding to one or more possible values of the breathing-related feature, with each group having an associated count that corresponds to the number of occurrences of a value or values for the breathing-related feature corresponding to the group;
apply a weighting to the count associated with one or more groups to form weighted counts by determining the weighted count for each group by subtracting a threshold value from a respective count; wherein weighted counts are set to zero in the event that the threshold value is equal to or greater than the respective count; and
determine the respiration rate from a mean of the histogram with the weighted counts.

9. An apparatus as claimed in claim 8, wherein the processing unit is configured to apply a weighting to the count associated with one or more groups such that the mean of the histogram is weighted towards the value or values of the breathing-related feature for the group having the highest count.

10. An apparatus as claimed in claim 8, wherein the processing unit is configured to apply a weighting to the count associated with one or more groups such that the value or values of the breathing-related feature for the group or groups having the highest counts are emphasized in the mean of the histogram.

11. An apparatus as claimed in claim 8, wherein the processing unit is configured to apply a weighting to the count associated with one or more groups by discarding from the histogram any group having a count that is less than a threshold number.

12. An apparatus as claimed in claim 8, wherein the processing unit is configured to apply a weighting to the count associated with one or more groups by determining the weighted count for each group as the nth power of the respective count, where n is any number greater than 1.

13. An apparatus as claimed in claim 8, wherein the apparatus comprises the sensor.

* * * * *